Figure 1:
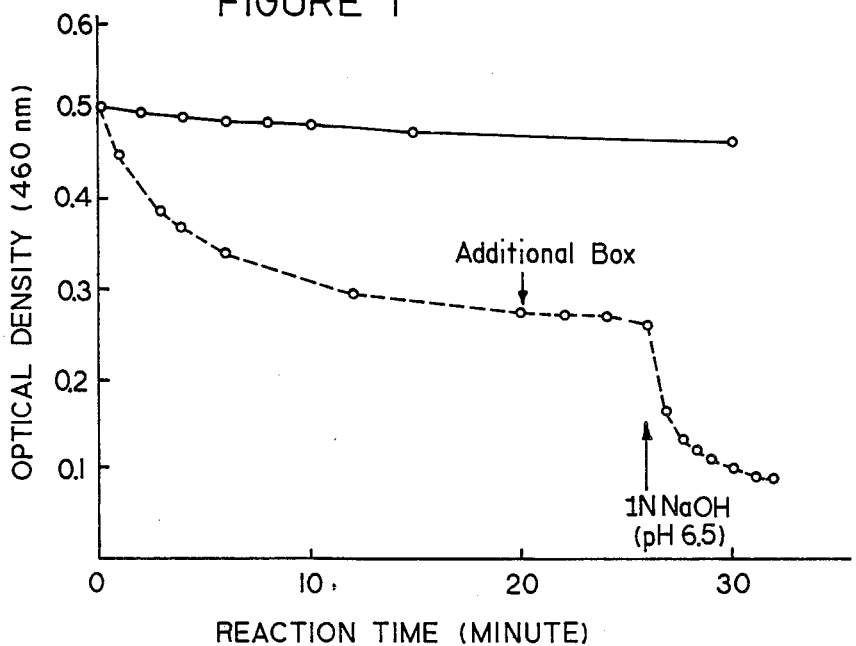

United States Patent [19]

Takayama et al.

[11] Patent Number: 4,571,383

[45] Date of Patent: Feb. 18, 1986

[54] REAGENT FOR MEASURING DIRECT BILIRUBIN BY ENZYMATIC METHOD AND METHOD FOR MEASUREMENT THEREOF

[75] Inventors: Masaharu Takayama, Ibaraki; Seiichi Taniguchi, Neyagawa; Masayasu Enomoto; Masahiro Muramoto, both of Takatsuki, all of Japan

[73] Assignee: Nippon Shoji Kaisha, Ltd., Osaka, Japan

[21] Appl. No.: 562,741

[22] Filed: Dec. 19, 1983

[30] Foreign Application Priority Data

Dec. 29, 1982 [JP] Japan .............................. 57-230125

[51] Int. Cl.$^4$ .............................................. C12Q 1/26
[52] U.S. Cl. .......................................... 435/25; 435/4
[58] Field of Search ....................... 435/4, 25; 436/97

[56] References Cited

PUBLICATIONS

Murao et al.—Chem. Abst., vol. 96, (1982), p. 64651c.

*Primary Examiner*—Sam Rosen
*Attorney, Agent, or Firm*—Wegner & Bretschneider

[57] ABSTRACT

Reagent for the measurement of direct bilirubin comprising a buffer solution having a pH range of 3.5 to 4.5 which contains bilirubin oxidase, preferably in the form of a test kit consisting essentially of (i) a buffer solution having a pH range of 3.5 to 4.5, (ii-a) a lyophilized bilirubin oxidase, (ii-b) a buffer solution for dissolving the lyophilized bilirubin oxidase, and (iii) a standard serum containing a prescribed amount of bilirubin, and a method for measurement of direct bilirubin by using the reagent. The reagent and method are useful for diagnosis of various diseases, for example, various hepatic diseases (e.g. jaundice) and cholepathia.

10 Claims, 4 Drawing Figures

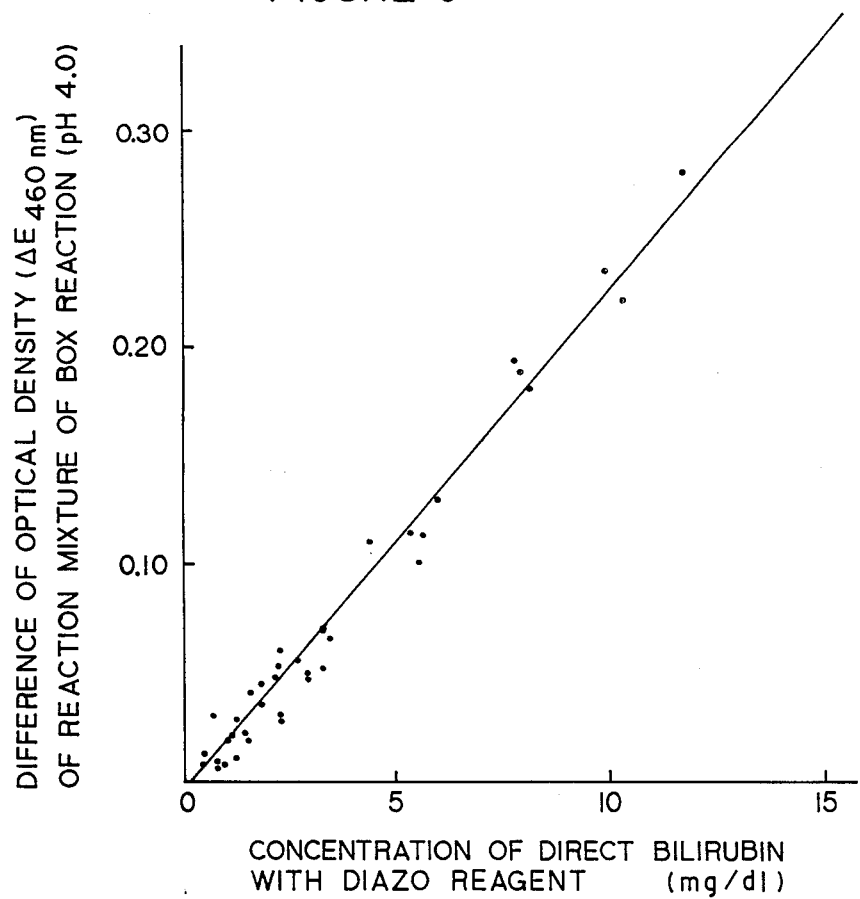

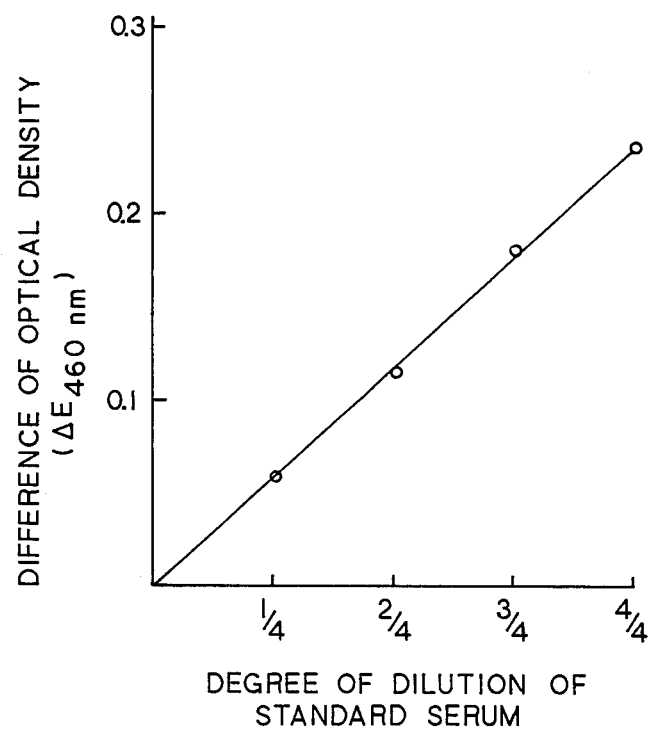

REAGENT FOR MEASURING DIRECT BILIRUBIN BY ENZYMATIC METHOD AND METHOD FOR MEASUREMENT THEREOF

The present invention relates to a reagent for measuring direct (conjugate) type bilirubin by an enzymatic method and a method for the measurement thereof.

Bilirubin is a representative pigment in vivo which is mainly derived from hemoglobin produced by decomposition of senescent erythrocytes. The free type bilirubin is occasionally converted into a protein-bound type bilirubin or a conjugate type bilirubin with glucuronic acid by the microsomal enzyme in liver and is excreted from the liver cell into the bile and further moved into intestinal tract. The bilirubin moved into intestinal tract is partially absorbed and circulates within intestine and liver, but most thereof is excreted outside the body in the form of urobilin. When the above step of from the production to excretion is disordered or changed, the blood level of bilirubin is increased to induce finally jaundice. Accordingly, when the blood level of bilirubin is measured, the data can be used for diagnosis of some diseases, for example, hepatic diseases and cholepathia, and hence, the measurement of bilirubin in blood has been clinically employed.

Bilirubin is usually either in a free type and protein-bound type (it is also called as non-conjugate or indirect type), or in a direct type (it is also called as conjugate type), as mentioned above. The direct type bilirubin (hereinafter, referred to as "direct bilirubin") has a structure that glucuronic acid binds to the propionic side chain of the free (or indirect) type bilirubin (hereinafter, referred to as "indirect bilirubin"), wherein the compound bound with one glucuronic acid is called as "monoglucuronide" and the compound bound with two glucuronic acids are called as diglucuronide". Both of the direct bilirubin and indirect bilirubin are totally called as total bilirubin.

In clinical test, there are usually measured the total bilirubin and direct bilirubin, and the indirect bilirubin is calculated by deducting the amount of direct bilirubin from that of total bilirubin. These two types of bilirubin have the following relation with diseases. For example, in acute obstructive jaundice, direct bilirubin (diglucuronide) is increased in blood; in parenchymal jaundice (hepatocellular decomposition), direct bilirubin (monoglucuronide) is increased in blood; and in hemolytic jaundice, indirect bilirubin is increased in blood. Thus, it is very important to measure direct bilirubin as well as total bilirubin for differential diagnosis of jaundice.

The blood bilirubin is usually measured by a colorimetry with a diazo reagent prepared by the method of Malloy-Evelyn [cf. Malloy, H.T. and Evelyn, K.A., J. Biol. Chem., 119, 481 (1937)]. However, according to this method, diglucuronide among the direct bilirubin is rapidly diazotized (because of this, it is also called as "one minute bilirubin"), but on the other hand, monoglucuronide is reacted slowly (because of this, it is also called as "delayed direct reaction bilirubin"), and hence, unless the time of diazotization reaction is measured precisely, the direct bilirubin can not be measured precisely.

Recently, a method for measuring bilirubin with an enzyme has been developed; for example, a method using hydrogen peroxide and peroxidase by Jacobson et al. [cf. Jacobson, J. & Wennberg, R. P., Clin. Chem., 20, 783 (1974)], a method of measuring decrease of yellow color owing to bilirubin by using mashroom-origin bilirubin oxidase by Tai-Wing Wu [cf. U.S. Pat. No. 4,211,844). Besides, Murao et al. reported that bilirubin oxidase was obtained from *Myrothecium verrucaria MT*-1 [cf. Murao, S. & Tanaka, N.; Agrical. Biol. Chem., 45 (10), 2383–2384 (1981), and Japanese Patent First Publication No. 159487/1982].

Such an enzymatic method is excellent in view of accurate measurement of bilirubin, but this method is disadvantageous in that only total bilirubin can be measured, but direct bilirubin can not be measured. As to the measurement of direct bilirubin by an enzymatic method, Kosaka et al. have reported that total bilirubin and direct bilirubin could be measured by reacting Myrothecium-origin bilirubin oxidase (obtained by Murao et al as mentioned above) in the presence and absence of sodium dodecylsulphate (SDS) and sodium cholate respectively at pH 8.6 [cf. Kosaka, Akira et al.; The Japanese Journal of Clinical Pathology, 30 (Suppl.), 123 (1982)]. The measurement of direct bilirubin by this method is based on the assumption that bilirubin oxidase does entirely not react with protein-bound bilirubin, but according to experiment by the present inventors, the reaction between them may occur.

The present inventors have intensively studied on an improved method for measuring direct bilirubin precisely and effectively by using Myrothecium-origin bilirubin oxidase and have found that the direct bilirubin can be measured by reacting them at a lower pH range, i.e. pH 3.5 to 4.5, while the optimum pH range of the bilirubin oxidase is at round pH 8.0.

An object of the present invention is to provide an improved method for measuring direct bilirubin by an enzymatic method using bilirubin oxidase, particularly Myrothecium-origin bilirubin oxidase. Another object of the invention is to provide a reagent useful for the measurement of direct bilirubin. These and other objects and advantages of the present invention will be apparent to persons skilled in the art from the following description.

The measurement of direct bilirubin by the present invention is carried out by treating a bilirubin-containing test sample with bilirubin oxidase to oxidize the yellow color bilirubin to green color biliverdin at the specified pH range, wherein decrease of yellow color of bilirubin is measured by colorimetry. In this method, when the reaction is carried out at pH 3.5 to 4.5, the free type, indirect bilirubin does not react with the enzyme and only the conjugate type, direct bilirubin can almost completely oxidized with the enzyme, and hence, the direct bilirubin can directly be measured with high precision by colorimetry.

According to the present invention, a measurement of the direct bilirubin is practically carried out by dissolving bilirubin oxidase in a buffer solution having the specified pH range, i.e. pH 3.5 to 4.5, preferably about 4.0, and reacting a bilirubin-containing serum test sample, followed by subjecting the reaction mixture to a conventional colorimetry. The reaction is carried out under the conventional reaction conditions, for example, at a temperature of 25° to 45° C., preferably at about 37° C., for a period of 10 to 30 minutes, preferably about 15 minutes.

The buffer solution includes any conventional buffer solutions having a pH value in the range of 3.5 to 4.5, for example, citric acid-phosphoric acid buffer, citric acid-acetic acid buffer, citric acid-sodium citrate buffer, citric acid-lactic acid buffer, citric acid-tartaric acid buffer, tartaric acid-sodium hydroxide buffer, tartaric acid-lactic acid buffer, tartaric acid-phosphoric acid buffer, and the like. Bilirubin oxidase is usually used in an amount of 1 to 10 units/test, preferably 2 to 5 units/test. The reagent (i.e. the bilirubin oxidase-containing buffer solution) is usually used in a small volume, e.g. 3 to 5 ml per one test, and hence, the bilirubin oxidase is dissolved in the buffer solution in an amount of 0.2 to 4 units/ml of the buffer, preferably 0.4 to 2 units/ml of the buffer. It has also been found by the present inventors that when potassium ferricyanide is used together, the amount of bilirubin oxidase can be decreased. For example, when potassium ferricyanide is used in an amount of 10 to 500 μM/test (0.002 to 0.2 mg/ml of buffer), the amount of bilirubin oxidase can be decreased to 0.025 to 3 unit/test (i.e. 0.005 to 0.6 unit/ml of buffer).

The unit of bilirubin oxidase is measured by the method disclosed in the above-mentioned Japanese Patent First Publication No. 159487/1982.

The colorimetry can be done by a conventional method, for example, by measuring the optical density of the reaction mixture at a wavelength of 460 nm against purified water using a commercially available spectrophotometer (e.g. Shimadzu type 220 double beam spectrophotometer, manufactured by Shimadzu Seisaku-sho, Japan). As a reference, a serum sample containing prescribed amount (known concentration) of bilirubin (it is hereinafter referred to as "standard bilirubin") is used, and the optical density thereof is measured likewise. Moreover, as a blank test sample, a test serum sample and a standard bilirubin which are each mixed with a buffer containing no bilirubin oxidase are also subjected to the measurement of the optical density, likewise. Based on the data in each measurement, the level of direct bilirubin in the test serum sample (mg/dl) is calculated by the following formula [I]:

$$\text{Concentration of direct bilirubin (mg/dl)} = \frac{A_B - A_T}{A_{SB} - A_{ST}} \times X \quad [I]$$

wherein $A_B$: Optical density of test serum sample (Blank test sample)

$A_T$: Optical density of test serum sample (which was reacted with the enzyme)

$A_{SB}$: Optical density of standard bilirubin (Blank standard sample)

$A_{ST}$: Optical density of standard bilirubin (which was reacted with the enzyme)

X: Concentration of direct bilirubin in the standard bilirubin (mg/dl)

The operation for the above measurement is explained below in more detail.

As the blank test sample, to a test serum sample is added a buffer solution (e.g. 100 mM citric acid-phosphoric acid buffer, pH 4.0), and the mixture is incubated (for example, at 37° C. for 15 minutes), and the resulting mixture is subjected to the measurement of optical density ($A_B$) at 460 nm against purified water. Separately, as the test sample reacted with the enzyme, to the same test serum sample is added an enzyme solution, i.e. the same buffer solution as above except that a prescribed amount of bilirubin oxidase is dissolved therein, and the mixture is incubated likewise, and then subjected to the measurement of optical density ($A_T$) at 460 nm against purified water. Besides, as the standard and blank standard sample, the above procedure is repeated except that standard bilirubin is used instead of the test serum sample, that is, the standard bilirubin is admixed with the same buffer solution or enzyme solution as used above and then incubated, and then the resulting solutions are each subjected to the measurement of optical density ($A_{SB}$ and $A_{ST}$) against purified water, respectively.

The reagent for measuring direct bilirubin of the present invention comprises substantially a buffer solution of pH 3.5 to 4.5 which contains 1 to 10 units/test of a bilirubin oxidase, which is used together with a usual buffer solution of pH 3.5 to 4.5 as mentioned hereinbefore and a standard bilirubin. From the practical viewpoint, it is preferably in the form of a test kit consisting of (i) a buffer solution containing no bilirubin oxidase, (ii) an enzyme solution containing bilirubin oxidase, and (iii) a serum containing a prescribed amount (known concentration) of direct bilirubin (standard bilirubin).

Besides, the enzyme solution (ii) is usually prepared immediately before used in view of less stability of the enzyme (bilirubin oxidase) by adding a lyophilized enzyme with a buffer solution for dissolving the enzyme. Said buffer solution is substantially the same as the buffer solution (i). Thus, in the reagent of the kit form, the enzyme solution (ii) consists of (ii-a) a lyophilized enzyme, and (ii-b) a buffer solution for dissolving the enzyme.

The lyophilized enzyme (ii-a) is usually prepared by dissolving a bilirubin oxidase of a prescribed amount (e.g. 1 to 10 units/test, i.e. 0.2 to 4 units/ml; when potassium ferricyanide is used together, 0.025 to 3 units/test, i.e. 0.005 to 0.6 unit/ml) in a purified water (e.g. 30 to 50 ml) in a container, optionally adding thereto a conventional carrier such as lactose and further optionally regulating the pH to 7.0 to 8.0 at which the enzyme can be kept stably, and then lyophilizing by a conventional method.

Moreover, the standard bilirubin (iii) may also optionally be lyophilized in a vial, and in such a case, the lyophilized standard bilirubin is re-dissolved in purified water when used. The lyophilization of the standard bilirubin can be done by a conventional lyophilization method. In the standard bilirubin (iii), the direct bilirubin is usually contained in an amount of 0.05 to 0.2 mg/ml. The solutions (i) and (ii-b) are also usually packed in a bottle. These reagents (i), (ii-a), (ii-b) and (iii) are usually packaged together in a single package as a test kit. They may also be packaged separately for the purpose of auto analysis. The size of each vial or bottle in the kit is not specified, but the reagents (ii-a) and (iii) are usually entered in a vial in a volume of 5 to 30 ml, and the solutions (i) and (ii-b) are entered in a bottle in a volume of 30 to 150 ml.

The reagents of the present invention, i.e. the buffer solution (ii-b) as well as other reagents (i) and (iii) may optionally be incorporated with conventional stabilizers, surfactants, antiseptics, or the like, unless disadvantageous effect is given on the reaction with the enzyme and also the subsequent measurement of optical density.

The following experiments were carried out in order to study the effect of the present invention in the measurement of direct bilirubin at various pH values.

Experiments

Enzyme, Reagents and Device for analysis:

Myrothecium-origin bilirubin oxidase (manufactured by Amano Seiyaku K.K., Japan) was used as bilirubin oxidase (hereinafter, it is abbreviated as "Box"), and 100 mM citric acid-phosphoric acid buffer (pH 3.0–6.0), 100 mM phosphate buffer (pH 6.5, 6.8, 7.0, 7.2 and 7.5), 100 mM tris-HCl buffer (pH 8.0, 8.5 and 9.0), and 100 mM carbonate buffer (pH 9.5 and 10.0) were used as a buffer solution. The control serum containing direct bilirubin was a bilirubin control serum (manufactured by Hyland Co.), and the standard bilirubin was bilirubin crystalline (manufactured by ICN Co.). Shimadzu type 220 double beam spectrophotometer (manufactured by Shimadzu Sheisakusho, Japan) was used for analysis.

Method:

To various buffer solutions as mentioned above were each added the bilirubin control serum and further Box, and the mixture was reacted at 37° C., while measuring the optical density at 460 nm with lapse of time.

It was confirmed whether the bilirubin tested was direct type or indirect type by the following procedure.

The bilirubin control serum was treated with chloroform to remove the indirect bilirubin, and the remaining bilirubin was reacted with Box. Separately, in accordance with a modified method of Manabe [cf. Manabe, Yukio; Igaku-to-Seibutsugaku (Medicine and Biology), 78, 73 (1969)], the bilirubin was fractionated, and as to each bilirubin fraction, the reactivity with Box was tested. Moreover, according to a modified method of Michaelsson [cf. Michaelsson, M; Scan. J. Clin. Lab. Invest., Suppl., 56 (1961)], total bilirubin and direct bilirubin were measured.

The reactivity of indirect bilirubin with Box was tested by adding bilirubin crystalline to 5% albumin solution and then subjecting the mixture to oxidation reaction with Box.

Experiment 1

(Relation between pH value and reactivity with Box)

Using above-mentioned buffer solutions having various pH ranges, bilirubin and Box were reacted.

As a result, in the range of pH 3.0 to less than 3.5, the oxidation reaction did almost not proceed, which suggested that Box did not show the activity at these pH ranges. On the other hand, in the range of pH 5.0 to 10.0, the reaction proceeded gradually continuously, and finally all bilirubins were oxidized, and hence, it is assumed that at the pH range all bilirubins (whether or not they are in direct type or in indirect type) are reactive with Box.

On the contrary, in the range of pH 3.5 to 4.5, the reaction proceeded comparatively rapidly, and the reaction was completed after a certain period of reaction time, and even when the reaction was continued for more time, the reaction became equilibrium, and even when additional Box was added to the reaction system, no more reaction proceeded. For example, to a test serum sample containing bilirubin (18 mg/dl) was added a citric acid-phosphoric acid buffer (pH 4.0) containing Box (2 units/test), and the mixture was reacted at 37° C., while measuring the optical density. The relation of the optical density measured and the lapse of time in the above procedure is graphed as shown in the accompanying FIG. 1. In FIG. 1, the solid line shows the case of blank test (i.e. the test sample was treated likewise except that a buffer solution containing no Box was used), and the dotted line shows the case of being reacted with Box.

As is clear from FIG. 1, when the reaction with Box was carried out at pH 4.0, the reaction became equilibrium after about 20 minutes, and even when an additional Box was added, the equilibrium did not changed. On the contrary, when 1 N NaOH was added to regulate the reaction system to pH 6.5 or more, the reaction proceeded again immediately, and the remaining bilirubin was completely oxidized after about 10 minutes.

Experiment 2

(Chemical types of bilirubin being capable to be oxidized at pH 3.5 to 4.5)

In order to study which chemical type of bilirubin was reacted with Box at pH 3.5 to 4.5 in the above Experiment 1, the direct bilirubin and indirect bilirubin were divided by fractionating into water and chloroform, and as to the bilirubin in the aqueous phase (i.e. direct bilirubin), the reactivity with Box was tested.

Figure 2:
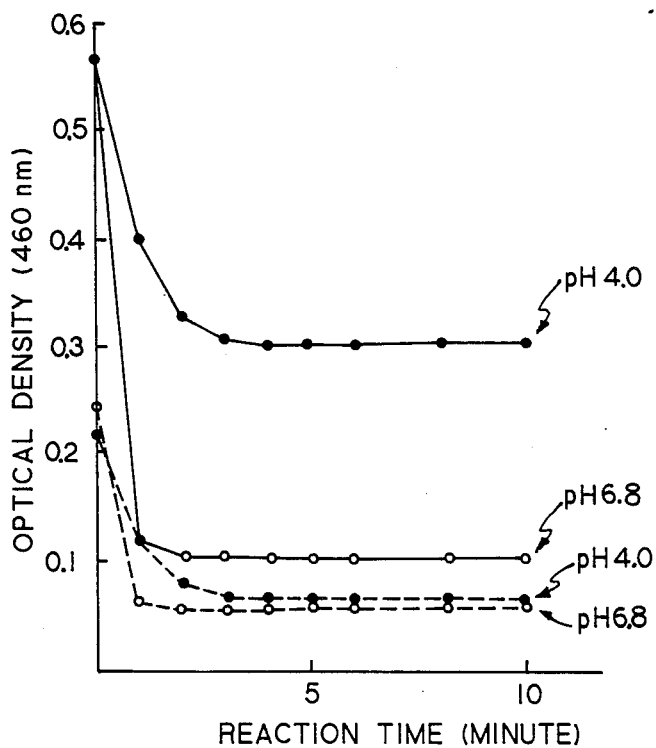

That is, the bilirubin control serum re-dissolved in water was treated with 5 times by volume of chloroform to separate into an aqueous phase and a chloroform phase, and the aqueous phase was further treated with chloroform to remove completely indirect bilirubin from the aqueous phase. The aqueous phase thus obtained was added to 100 mM citric acid-phosphoric acid buffer (pH 4.0) and 100 mM phosphate buffer (pH 6.8), and to each buffer solution was Box added. As a control, the bilirubin control serum was reacted likewise without being treated with chloroform. These reaction mixtures were subjected to the measurement of an optical density at 460 nm, and the relation between the optical density and the lapse of reaction time was graphed, which is shown in the accompanying FIG. 2. In FIG. 2, the solid line shows the case of non-treatment with chloroform, and the dotted line shows the case of treatment with chloroform.

As is clear from FIG. 2, in case of non-treatment with chloroform, the reaction with Box at pH 4.0 proceeded about 60% of the reaction at pH 6.8, but on the other hand, in case of treatment with chloroform, the reaction with Box proceeded appropriately equally both in pH 4.0 and in pH 6.8. This fact means that at pH 4.0 the direct bilirubin was almost completely oxidized with Box.

Experiment 3

It was clear from the above Experiment 2 that the direct bilirubin was almost completely oxidized at pH 4.0, but it is still not clear whether the indirect bilirubin is attacked by Box and how degree of reaction proceeds. In order to make clear them, according to a modified method of Manabe as mentioned above, the bilirubins were fractionated likewise into Fraction I: protein-bound bilirubin (indirect bilirubin), Fraction II: glucuronic acid-conjugate type bilirubin (direct bilirubin), Fraction III: non-conjugate type bilirubin (indirect bilirubin), and Fraction IV: other types of bilirubin, and these fractions were each reacted with Box at pH 4.0 and pH 6.8 in the same manner as described in Experiment 2. As a result, all fractions reacted with Box at pH 6.8, but only Fraction II reacted with Box at pH 4.0 (other fractions did almost not reacted).

Besides, as to a commercially available bilirubin crystalline (manufactured by ICN Co.) which is known to be mostly indirect bilirubin, the reaction with Box was done at pH 4.0. As a result, no reaction proceeded.

Experiment 4

In the same manner as described in Experiment 2, test samples containing various concentrations of bilirubin were reacted with Box at pH 4.0, 37° C. for 20 minutes, and then the optical density at 460 nm was measured. The data were compared with those of direct bilirubin which were obtained by measuring the same test samples with a known diazo reagent (Bilirubin Kit-N, manufactured by Nippon Shoji K.K., Japan), and the correlation between them was graphed as shown in the accompanying FIG. 3. As is clear from FIG. 3, both data are almost correlative with each other.

As is clear from the above experiments, according to the method of the present invention, even when the test samples containing various types of bilirubins are reacted with bilirubin oxidase at pH 3.5 to 4.5, only direct bilirubin can react with the enzyme, and by comparing the optical density of the reaction mixture with that of standard bilirubin, the concentration of direct bilirubin in the test sample can readily be calculated.

Thus, the reagent and method of the present invention are very effective for measuring bilirubin, particularly direct bilirubin, in serum samples to be tested and hence are very useful for diagnosis of various diseases, for example, hepatic diseases and cholepathia.

The reagent of the present invention and method for measuring direct bilirubin by the present invention are illustrated in the following examples.

EXAMPLE 1

Buffer solution:

100 mM Citric acid-phosphoric acid buffer (pH 3.5, 3.7, 3.8, 3.9, 4.0, 4.1, 4.2, 4.3, and 4.5), and 100 mM phosphate buffer (pH 6.8) (as a reference) were used.

Enzyme solution for reaction:

To each buffer solution as mentioned above was added Myrothecium-origin bilirubin oxidase (manufactured by Amano Seiyaku K.K., Japan, 2.5 units/test) to give the enzyme solution.

Standard bilirubin:

A serum containing direct bilirubin (8.04 mg/dl) was used.

Reaction and result:

To the bilirubin-containing test serum (100 μl) was added each buffer solution (3.0 ml), and the mixture was incubated at 37° C. for 15 minutes, and the optical density of the reaction mixture at 460 nm was measured with Shimadzu type 220 double beam spectro-photometer against purified water. The above procedure was repeated except that the enzyme solution was used instead of the buffer solution, and the optical density of the reaction mixture was measured likewise. Besides, the above procedure was also repeated except that the standard bilirubin was used instead of the test serum, and the optical density was measured likewise.

These results are shown in Table 1. Besides, the concentration of direct bilirubin was calculated from these data in accordance with the formula [I] shown hereinbefore. It is also shown in Table 1.

TABLE 1

| | | Optical density (460 nm) | | | | |
|---|---|---|---|---|---|---|
| | | Test serum sample | | Standard bilirubin | | |
| No. | pH of enzyme solution | Reacted with enzyme | Non-reacted with enzyme | Reacted with enzyme | Non-reacted with enzyme | Concentration of direct bilirubin (mg/dl) |
| 1 | 3.5 | 0.155 | 0.178 | 0.261 | 0.314 | 3.5 |
| 2 | 3.7 | 0.150 | 0.181 | 0.241 | 0.311 | 3.6 |
| 3 | 3.8 | 0.142 | 0.188 | 0.229 | 0.336 | 3.5 |
| 4 | 3.9 | 0.138 | 0.198 | 0.208 | 0.349 | 3.4 |
| 5 | 4.0 | 0.133 | 0.207 | 0.196 | 0.366 | 3.5 |
| 6 | 4.1 | 0.111 | 0.191 | 0.177 | 0.359 | 3.5 |
| 7 | 4.2 | 0.108 | 0.192 | 0.172 | 0.366 | 3.5 |
| 8 | 4.3 | 0.130 | 0.216 | 0.184 | 0.380 | 3.5 |
| 9 | 4.5 | 0.125 | 0.221 | 0.166 | 0.380 | 3.6 |
| 10 | 6.8 | 0.101 | 0.216 | 0.101 | 0.304 | — |

EXAMPLE 2

By the same procedure as described in Example 1, the optical density of bilirubin control and serum of a patient was measured continuously ten times by using the same reagents as used in Example 1, and the difference of the optical density between them was calculated. The results are shown in Table 2. As is clear from the results, the method showed good reproducibility, and hence, it was confirmed that the method of the present invention has high precision.

TABLE 2

| No. | Bilirubin control | Serum of patient |
|---|---|---|
| 1 | 0.242 | 0.241 |
| 2 | 0.244 | 0.245 |
| 3 | 0.239 | 0.234 |
| 4 | 0.244 | 0.241 |
| 5 | 0.240 | 0.241 |
| 6 | 0.238 | 0.234 |
| 7 | 0.247 | 0.244 |
| 8 | 0.241 | 0.241 |
| 9 | 0.239 | 0.235 |
| 10 | 0.246 | 0.243 |
| Average | 0.242 | 0.240 |
| Standard deviation | 0.00313 | 0.00408 |
| Coefficient of variation | 1.29% | 1.70% |

REFERENCE EXAMPLE (Preparation of calibration curve)

(1) Preparation of test solution

Buffer solution: 0.1 M Citric acid-phosphoric acid buffer (pH 4.0)

Enzyme solution for reaction: It was prepared by adding Myrothecium-origin bilirubin oxidase (manufactured by Amano Seiyaku K.K., Japan; 2.5 units/test) to 0.1 M citric acid-phosphoric acid buffer (pH 4.0).

(2) Preparation of standard bilirubin

It was prepared by dissolving bilirubin control in a liquid for dissolution attached thereto and diluted with a physiological saline solution in a dilution fold of 1/4, 2/4, 3/4 and 4/4.

(3) Procedure of measurement

Four test tubes were each charged with the above standard bilirubin (each 100 μl) having various concentrations, and thereto was added the above enzyme solution (3.0 ml). The mixture was reacted at 37° C. for 15 minutes, and then the optical density of the reaction mixture [Est(B)] was measured against purified water. Based on the data thus obtained, there was calculated the difference of the optical density between the standard sera having different concentrations:

$$\Delta E_{460nm}[=Est(B)-Est]$$

and based on the resulting data, a calibration curve was drawn. It is shown in the accompanying FIG. 4. As is shown in the figure, there was obtained a direct line passing through the origin, by which it was confirmed that the method of the present invention can be used for quantitative determination of bilirubin.

EXAMPLE 3

(A) Preparation of reagents:
(i) Blank buffer solution:

Citric acid trisodium salt (2.94 g) was dissolved in purified water (80 ml) and thereto was added lactic acid (3.93 g), and the mixture was regulated to pH 3.7 with lactic acid or sodium hydroxide, and then, the mixture was made total 100 ml by adding purified water thereto.

(ii) Buffer solution for dissolving enzyme:

The same as the above blank buffer solution.

(iii) Enzyme (lyophilized product):

Potassium ferricyanide (8.23 mg) was dissolved in purified water (80 ml) and therein was dissolved bilirubin oxidase (1,700 units), and thereto was added purified water so as to make totally 100 ml. Each 2 ml of this solution was entered into a 5 ml vial and lyophilized.

This lyophilized product was re-dissolved with 50 ml of the buffer solution for dissolving enzyme (ii) as mentioned above to give an enzyme solution, when used.

(iv) Standard bilirubin (lyophilized product):

To human pooled serum (80 ml) was added a free bilirubin solution (2 ml) which was prepared by dissolving sodium carbonate (159 mg) in purified water (8 ml) and dissolving therein bilirubin crystalline (50 mg) and adding purified water so as to make totally 10 ml. To the mixture was added a conjugate bilirubin solution (2 ml) which was prepared by dissolving conjugate bilirubin (75 mg) in purified water (10 ml). To the resulting mixture was added purified water so as to make totally 100 ml. Each 2.0 ml of this mixture was entered in a 5 ml vial and lyophilized. The concentration of direct bilirubin was determined with Bilirubin Kit-N (manufactured by Nippon Shoji K.K., Japan). and found 7.5 mg/dl.

This lyophilized product was re-dissolved with purified water (2.0 ml) to give a standard bilirubin solution, when used.

(B) Measurement of direct bilirubin with the above reagents:

Into four 10 ml volume test tubes (1), (2), (3) and (4), blank buffer solution or enzyme solution prepared in the above (A), (i) and (iii) in a volume as shown in Table 3. Each test tube was warmed at 37° C. for 5 minutes, and thereto was added test serum or standard bilirubin solution prepared in the above (A), (iv) in the volume as shown in Table 3. The mixture was mixed well and reacted at 37° C. for 20 minutes. The reaction mixture was subjected to measurement of optical density at 460 nm. The data are also shown in Table 3. Based on the optical densities thus obtained, the concentration of bilirubin (mg/dl) was calculated in accordance with the formula [I] hereinbefore. As a result, the test serum contained the direct bilirubin of 5.1 mg/dl.

TABLE 3

| Reagent | Test tube (1) | Test tube (2) | Test tube (3) | Test tube (4) |
| --- | --- | --- | --- | --- |
| Blank buffer solution | — | 3.0 ml | — | 3.0 ml |
| Enzyme solution | 3.0 ml | — | 3.0 ml | — |
| Test serum | 100 μl | 100 μl | — | — |
| Standard bilirubin solution | — | — | 100 μl | 100 μl |
| Optical density | 0.310 | 0.420 | 0.297 | 0.460 |

What is claimed is:

1. A diagnostic test kit having component reagents packaged together in a single package; the kit comprising the combination of a buffer solution having a pH range of 3.5 to 4.5, a lyophilized bilirubin oxidase, a buffer solution for dissolving the lyophilized bilirubin oxidase, and a standard serum containing a prescribed amount of bilirubin.

2. The kit according to claim 1, wherein the lyophilized bilirubin oxidase contains 1 to 10 units/test of bilirubin oxidase.

3. The kit according to claim 1, wherein the lyophilized bilirubin oxidase contains 0.025 to 3 units/test of bilirubin oxidase and also 10 to 500 μM/test of potassium ferricyanide.

4. A method for measurement of direct bilirubin, which comprises reacting a test serum sample with bilirubin oxidase in a buffer solution of pH 3.5 to 4.5.

5. The method according to claim 4, wherein the buffer solution has about pH 4.0.

6. The method according to claim 4, wherein the reaction with bilirubin oxidase is carried out at 37° C. for 10 to 30 minutes, followed by measuring the optical density of the reaction mixture at a wavelength of 460 nm.

7. A reagent for measurement of direct bilirubin, which comprise a lyophilized bilirubin oxidase and a buffer solution for dissolving the lyophilized bilirubin oxidase, said buffer solution having a pH range of 3.5 to 4.5.

8. The reagent according to claim 7, wherein the lyophilized bilirubin oxidase contains 1 to 10 units/test of bilirubin oxidase.

9. The reagent according to claim 7, wherein the lyophilized bilirubin oxidase contains 0.025 to 3 units/test of bilirubin oxidase and also 10 to 500 μM/test of potassium ferricyanide.

10. The reagent according to claim 7, wherein the bilirubin oxidase is Myrothecium-origin bilirubin oxidase.

* * * * *